United States Patent
Mukai et al.

(10) Patent No.: US 8,357,141 B2
(45) Date of Patent: Jan. 22, 2013

(54) CATHETER HAVING RADIOPAQUE PORTION AND TRANSPARENT PORTION

(75) Inventors: Shoso Mukai, Fukuroi (JP); Masaki Ogawa, Fukuroi (JP)

(73) Assignee: Covidien AG (CH)

( * ) Notice: Subject to any disclaimer, the term of this patent is extended or adjusted under 35 U.S.C. 154(b) by 443 days.

(21) Appl. No.: 11/665,594

(22) PCT Filed: Oct. 18, 2005

(86) PCT No.: PCT/EP2005/011195
§ 371 (c)(1),
(2), (4) Date: May 7, 2008

(87) PCT Pub. No.: WO2006/042739
PCT Pub. Date: Apr. 27, 2006

(65) Prior Publication Data
US 2009/0088727 A1    Apr. 2, 2009

(30) Foreign Application Priority Data

Oct. 18, 2004    (JP) ................................. 2004-302749

(51) Int. Cl.
*A61M 25/098* (2006.01)
(52) U.S. Cl. ....................................... 604/529; 525/458
(58) Field of Classification Search .............. 604/523, 604/529, 524, 526; 600/424; 525/458
See application file for complete search history.

(56) References Cited

U.S. PATENT DOCUMENTS

| | | | | |
|---|---|---|---|---|
| 5,159,050 A | * | 10/1992 | Onwumere | 528/67 |
| 5,177,170 A | * | 1/1993 | Sarpeshkar et al. | 528/76 |
| 5,342,383 A | * | 8/1994 | Thomas | 606/19 |
| 5,947,940 A | * | 9/1999 | Beisel | 604/526 |
| 6,143,893 A | | 11/2000 | Tanzi et al. | |
| 6,152,912 A | | 11/2000 | Jansen et al. | |
| 6,200,338 B1 | * | 3/2001 | Solomon et al. | 623/1.34 |
| 6,623,823 B1 | * | 9/2003 | Onwumere | 428/36.91 |
| 2004/0131863 A1 | | 7/2004 | Belliveau et al. | |

FOREIGN PATENT DOCUMENTS

| | | |
|---|---|---|
| CN | 1260211 A | 7/2000 |
| JP | 06-172638 | 6/1994 |
| JP | 08-266617 | 10/1996 |
| JP | 2000-217903 | 8/2000 |
| JP | 2002-017860 | 1/2002 |
| WO | WO 03/066119 A1 | 8/2003 |

OTHER PUBLICATIONS

Office Action issued in corresponding Chinese Patent Application No. 200580041146.X dated Jun. 5, 2009.
Kaneko, Takashi, Seikei-Kakou (Molding Process), pp. 404-407, vol. 15, No. 6 (2003) (Abstract Only).
Ishikawa, Kenji, Gosei-Jushi (Synthetic Resin), pp. 29-32, vol. 44, No. 4 (1998) (Abstract Only).

* cited by examiner

*Primary Examiner* — Kevin C Sirmons
*Assistant Examiner* — Brandy C Scott
(74) *Attorney, Agent, or Firm* — John Paul Mello

(57) ABSTRACT

A catheter comprises a tubular body portion (11) including an elongate portion (13) made of a transparent material, and at least one substantially linear contrast-radiography portion (14a, 14b) made of an X-ray opaque material and extending in the longitudinal direction of the elongate portion. The body portion (11) is hollow to allow passage of a liquid therethrough. A majority of the transparent material is composed of an aromatic polyurethane, while the material forming the at least one contrast-radiography portion (14a, 14b) is a mixture composed at least mainly of the X-ray opaque material and an aliphatic polyurethane.

15 Claims, 2 Drawing Sheets

CATHETER HAVING RADIOPAQUE PORTION AND TRANSPARENT PORTION

This application claims the benefit of and priority to PCT Application No. PCT/EP2005/011195 filed on Oct. 18, 2005 (published as WO 2006/042739) which, in turn, claims the benefit of and priority to Japanese Application No. 2004-302749 filed on Oct. 18, 2004, the entire disclosures of each of which are hereby incorporated by reference herein.

TECHNICAL FIELD

The present invention relates to a catheter which may remain in the body of a patient for use in supplying the patient with a liquid such as a liquid chemical or liquid nourishment.

BACKGROUND ART

It is known to feed a person (hereinafter referred to as the "patient"), who has a reduced oral intake function as a result of aging or disease, with a liquid chemical or liquid nourishment in the form of a high-calorie transfusion through a blood vessel by means of a catheter. In some cases, for example as known from JP-U-51 108 389, the position of the catheter in the patient can be confirmed by incorporating an X-ray opaque material in the catheter body. Such a catheter is made of a flexible plastic tube with a portion of the tube incorporating an X-ray opaque material which extends around a circumferential portion of a wall of the plastic tube and also extends in an axial direction of the plastic tube. Consequently, when the catheter remains in a blood vessel of the patient, the position of the catheter can be confirmed using X-rays to identify the portion of the plastic tube containing the X-ray opaque material.

Polyurethane is generally used as the material for making such a catheter because it is strong and bio-compatible (by which it is meant that the material becomes soft in the body or is harmless to the body). More particularly, the polyurethane used in the catheter may be aliphatic polyurethane manufactured from aliphatic isocyanate or aromatic polyurethane manufactured from aromatic isocyanate. Of these, a catheter made from aliphatic polyurethane has excellent workability and bio-compatibility and softens when left in the body.

A catheter made of aliphatic polyurethane is hard when inserted into the body so that it is easy to insert, and becomes soft after it has been left in the body so that it has ideal operability and bio-compatibility. On the other hand, however, a catheter made of aliphatic polyurethane has lower chemical resistance so that it readily degrades when it contacts liquid chemicals. In recent years, anticancer medicines containing alcohol are frequently administered in the form of liquid chemicals with the result that catheters made of aliphatic polyurethane are not suitable in such situations.

On the other hand, a catheter made of aromatic polyurethane has excellent chemical resistance but has the disadvantages that it does not become soft after it has been left in the body, and that it does not blend as effectively with the X-ray opaque material. Consequently, only a small amount of X-ray opaque material can be mixed with aromatic polyurethane with the result that the catheter is difficult to identify by linear contrast radiography. As a result, when a catheter is made of aromatic polyurethane no transparent portion is formed in the catheter and the entire catheter incorporates the X-ray opaque material in order to be able to identify the catheter by linear contrast radiography. Because the catheter is not transparent, this gives rise to a problem in that the passage of the liquid chemical through the catheter cannot be confirmed.

OBJECT OF THE INVENTION

An object of the present invention is to provide a catheter which is easy to use, has good bio-compatibility and chemical resistance, is easy to identify by contrast radiography and has a transparent portion for confirming the passage of liquid therethrough.

SUMMARY OF THE INVENTION

According to the present invention there is provided a catheter comprising a tubular body portion including an elongate portion made of a transparent material, and at least one substantially linear contrast-radiography portion made of an X-ray opaque material and extending in the longitudinal direction of the elongate portion, the body portion being hollow to allow passage of a liquid therethrough, wherein a majority of the transparent material is composed of an aromatic polyurethane, and wherein the material forming the at least one contrast-radiography portion is a mixture composed at least mainly of the X-ray opaque material and an aliphatic polyurethane.

Aromatic polyurethane has excellent chemical resistance, especially to alcohol. As a result, the transparent portion of such a catheter does not deteriorate even if it contacts a liquid chemical, such as an anticancer medicine containing an alcohol such as ethanol or the like, over a long time. Because the linear contrast-radiography portions are composed mainly of aliphatic polyurethane which blends well with the X-ray opaque material and which softens when it remains in the body, the contrast-radiography portions can incorporate a relatively large proportion of X-ray opaque material. Consequently, contrast-radiography can be performed even though the contrast-radiography portions have a narrow linear shape. As a result, the size (or width or circumferential extent) of the transparent portion can be enlarged to facilitate confirmation of the passage of liquid through the catheter. Moreover, the linear contrast-radiography portions of the catheter are relatively hard when inserted into the body, but become soft if they remain in the body. Therefore, not only the operability at the insertion time, but also bio-compatibility, is improved as compared with the case in which the catheter is entirely made of aromatic polyurethane.

The at least one contrast-radiography portion may be enclosed in a wall portion forming the elongate portion. The at least one contrast-radiography portion may be embedded to a depth of at least 0.01 mm, preferably to at least 0.02 mm, and most preferably to substantially 0.04 mm. Thus, the linear contrast-radiography portions are not exposed at the surface and have no contact with liquid such as the liquid chemical so that they neither deteriorate nor become separated.

The transparent material forming the elongate portion may consist essentially of aromatic polyurethane.

Alternatively, the transparent material forming the elongate portion may comprise a mixture of aromatic polyurethane and aliphatic polyurethane. The transparent material forming the elongate portion may comprise from substantially 50% to substantially 80%, and preferably substantially 60%, aromatic polyurethane. Consequently, the transparent portion of the catheter may be provided with the characteristics of both aromatic polyurethane and aliphatic polyurethane. As a result, the catheter obtained has good chemical resistance, operability and bio-compatibility.

More than one, for example two, contrast-radiography portion may be provided.

The at least one contrast-radiography portion may comprise substantially 60% aliphatic polyurethane.

The X-ray opaque material may be selected from barium sulfate, bismuth subcarbonate, bismuth tungstate, tantalum tungstate and mixtures thereof.

The circumferential extent of the contrast-radiography portion(s) may be from substantially 10% to substantially 70% of the circumference of the elongate portion, and preferably may be substantially 60% of the circumference of the elongate portion.

For a better understanding of the present invention and to show more clearly how it may be carried into effect reference will now be made, by way of example, to the accompanying drawings in which:

DESCRIPTION OF PREFERRED EMBODIMENT

Figure 1:
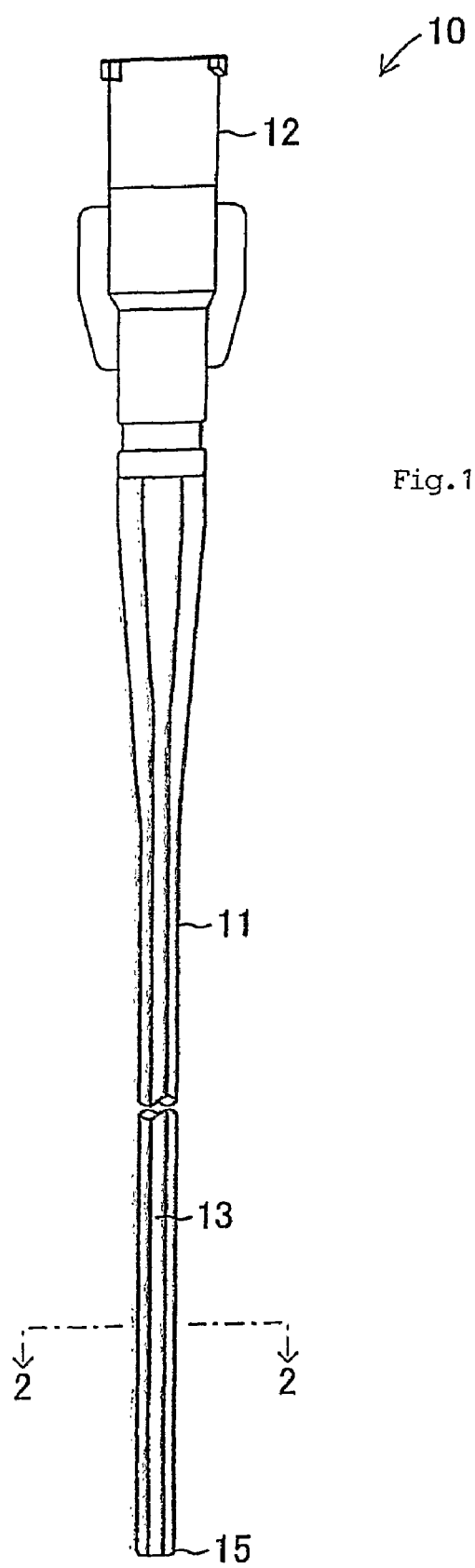
FIG. 1 is an elevational view of one embodiment of a catheter according to the present invention.
Figure 2:
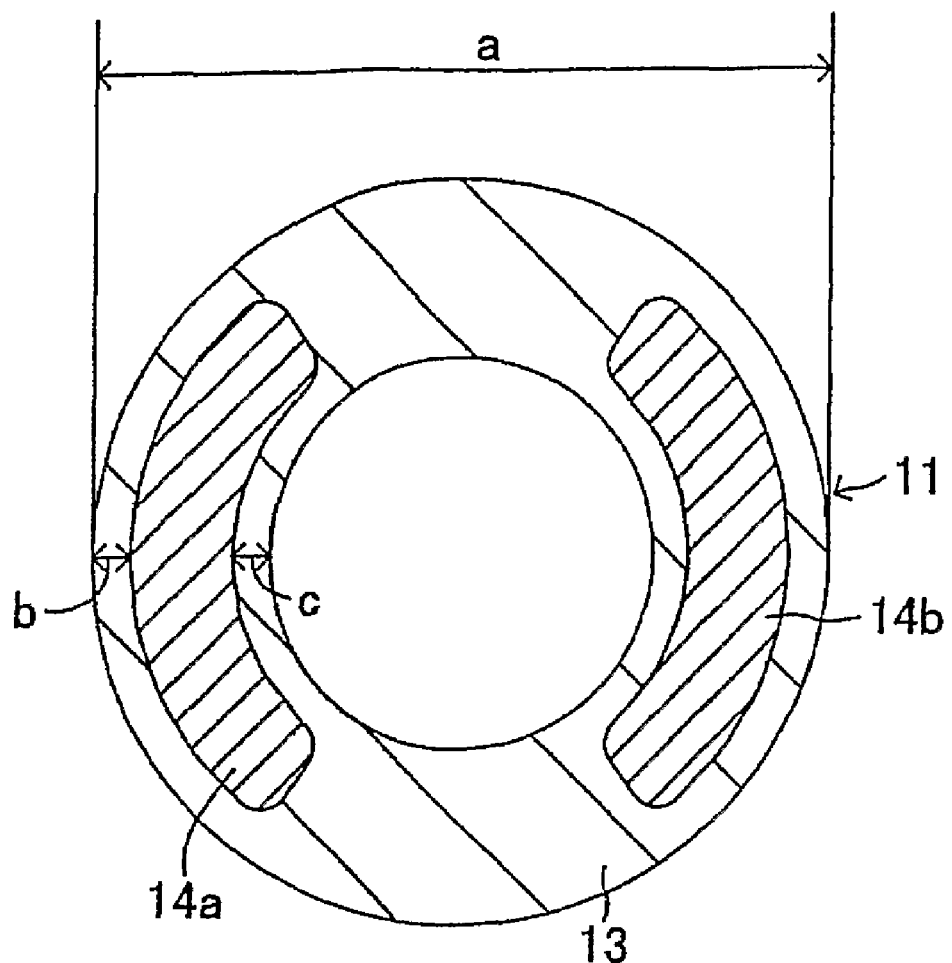
FIG. 2 is a sectional view along the line 2-2 of FIG. 1.

One embodiment of a catheter according to the present invention will be described with reference to the accompanying drawings. FIG. 1 and FIG. 2 show a catheter 10 which includes a catheter body 11 in the form of an elongated flexible tube, and a tube fixing portion 12. The catheter body 11 includes a cylindrical portion 13 which is generally transparent, but is provided with a pair of linear contrast radiography portions 14a and 14b arranged opposite each other within the wall of the cylindrical portion 13. The linear portions 14a and 14b are individually formed in a trough (or "U") shape as to extend partly around the circumference of the cylindrical portion 13 and in the longitudinal (axial) direction of the cylindrical portion 13.

The cylindrical portion 13 is made of a transparent material composed of a major proportion of aromatic polyurethane and a minor proportion of aliphatic polyurethane. On the other hand, the linear portions 14a and 14b are made of a suitable material such as white barium sulfate blended with aliphatic polyurethane. The tube fixing portion 12 comprises a tubular member made of a polyurethane resin or the like and is attached to the rear end of the catheter body 11. When a liquid such as a liquid chemical is to be fed into the catheter 10, the open end (located at the upper end region of FIG. 1) of the tube fixing portion 12 is connected to a transfusion line. At this time, the operator can manually operate the catheter 10 with the tube fixing portion 12.

In the illustrated embodiment, the external diameter (a) of the catheter body 11 (i.e., the external diameter of the portion shown in FIG. 2) is 16 G (i.e., 1.50 mm). The regions of the cylindrical portion 13 of the catheter body located radially externally and radially internally of the linear portions 14a and 14b, have thicknesses (b) and (c) of 0.04 mm. Moreover, the total angular proportion, as measured from the center of the catheter body 11 and divided by 360 degrees, of the regions formed by the linear portions 14a and 14b (i.e., due to the circumferential extent of the linear portions 14a and 14b is substantially 61%.

The transparent material forming the cylindrical portion 13 was a mixture of aromatic polyurethane and aliphatic polyurethane, the former of which is sold under the Trade Mark Tecothane (Noveon Inc.) and the latter of which is sold under the Trade Mark Tecoflex (Noveon Inc.). The aromatic polyurethane and the aliphatic polyurethane were mixed in a ratio of 60:40 (by weight or by volume) for use as the transparent material. On the other hand, the material forming the linear portions 14a and 14b was a mixture of aliphatic polyurethane and barium sulfate, the former of which is sold under the Trade Mark Tecoflex (Noveon Inc.). Moreover, the aliphatic polyurethane and the barium sulfate were blended in a ratio of 60:40 (by weight or by volume).

In use of the catheter 10, a blood vessel is first pierced with a cannula (not shown). Next, the catheter body 11 is gradually inserted, leading end portion 15 first, into the cannula which remains in the blood vessel as to reach a target position in the blood vessel. At this time, the catheter body 11 is sufficiently hard that it can be inserted easily.

Next, when the leading end portion 15 of the catheter 10 reaches the target position, the cannula is removed from the blood vessel. At this time, a precautionary step is taken to ensure the catheter 10 is not out of position, and a confirmation is made whether or not the leading end portion 15 of the catheter 10 is at the target position. This confirmation is effected with X-rays to image the contrast-radiography linear portions 14a and 14b, because the linear portions 14a and 14b are made of an X-ray opaque material.

Then, the injection of the liquid chemical or the like is commenced by connecting a predetermined transfusion line to the tube fixing portion 12 while the catheter 10 remains in the blood vessel. As a result, the predetermined liquid chemical or the like is transferred via the blood vessel into the body of a patient. It will be noted that a significant proportion of the catheter body 11 is not occupied by the contrast-radiography linear portions 14a and 14b so that it is possible to confirm the passage of the liquid chemical or the like through the catheter. The confirmation of the passage of the liquid chemical liquid or the like is effected by viewing the portion of the catheter body 11 positioned externally of the body of the patient.

It has been found that the catheter body 11 becomes soft when left in the body, for example due to body temperature or the like. As a result, the catheter body 11 does not damage the patient's body even if the catheter body 11 should move. Moreover, the catheter body 11 has excellent chemical resistance so that it does not deteriorate even if a liquid containing alcohol or the like is used as the liquid chemical or the like to be transferred into the body of the patient. As a result, the catheter can be employed for a significant time.

Thus, the catheter 10 is manufactured with the transparent portion 13 of its body 11 made of a transparent material blended from 60% (by weight or volume) of aromatic polyurethane having an excellent alcohol-resistance and 40% (by weight or volume) of aliphatic polyurethane having excellent bio-compatibility. As a result, the transparent portion 13 has the characteristics of both aromatic polyurethane and aliphatic polyurethane so that the catheter 10 can have excellent chemical resistance, operability and bio-compatibility. On the other hand, the contrast-radiography linear portions 14a and 14b are made of barium sulfate and aliphatic polyurethane which blends well with the barium sulfate so that the contrast-radiography linear portions 14a and 14b can contain a relatively high proportion of barium sulfate to improve the contrast of the radiographic image.

The linear portions 14a and 14b are enclosed within the transparent portion 13 so that they do not contact the liquid chemical or the like. As a result, the linear portions 14a and 14b neither deteriorate nor peel. Moreover, a significant clearance is provided between the contrast-radiography linear portions 14a and 14b in the catheter body 11 so that the passage of the liquid chemical or the like through the catheter body 11 can be confirmed. Further, the catheter body 11 of the catheter 10 is hard when inserted into the patient's body, but becomes soft after it has been left in the body, so that it provides excellent operability at the time of insertion and also provides excellent bio-compatibility.

EXAMPLES

Example 1 of the catheter 10 according to the present invention, the catheter having the composition and structure described above, and Comparison 1 in the form of a catheter having a transparent portion made only of aliphatic polyurethane were subjected to comparison tests for hardness and alcohol-resistance at 40° C. The results of these comparison tests are described below. The catheter of Comparison 1 had the same external diameter of 16 G (i.e., 1.50 mm) as the catheter body 11 of Example 1, as shown in Table 1. The regions of the cylindrical portion 13 of the catheter body located radially externally and radially internally of the linear portions 14a and 14b are 0.04 mm thick. Moreover, the linear portions have a circumferential extent of substantially 60% of the circumference of the cylindrical portion 13.

The material used to make the transparent portion of Comparison 1 was 100% aliphatic polyurethane sold under the Trade Mark Tecoflex (Noveon Inc.). On the other hand, similarly to catheter 10 the material used to make the contrast-radiography linear portions was a blend of 60% (by weight or volume) aliphatic polyurethane sold under the Trade Mark Tecoflex (Noveon Inc.) and 40% (by weight or volume) of barium sulfate. The results of comparison tests of hardness are presented as ratios calculated by dividing the modulus of elasticity of the catheter at 40° C. by the modulus of elasticity of the catheter at room temperature (25° C.). Comparison tests for alcohol resistance were evaluated by conducting a bending test 5 hours after the injection of 75% ethanol into the catheter and determining the number of times the catheter could be deformed before a crack appeared.

TABLE 1

| | Example 1 | Comparison 1 |
|---|---|---|
| Catheter Size | 16 G (external diameter: 1.50 mm) | 16 G (external diameter: 1.50 mm) |
| Cylindrical Portion | Tecothane/Tecoflex = 60/40 | Tecoflex: 100% |
| Contrast-Radiography Linear Portions | Tecoflex/barium sulfate = 60/40 | Tecoflex/barium sulfate = 60/40 |
| No. of Contrast-Radiography Linear Portions | 2 | 2 |
| Circumferential extent of Contrast-Radiography Linear Portions | 61% | 60% |
| Coating Yes-No/ Thickness | Yes (Out: 0.04 mm, In: 0.04 mm) | Yes (Out: 0.04 mm, In: 0.04 mm) |
| Hardness at 40° C. | 28% | 25% |
| Alcohol-Resistance | ≧500 times | 182 times |

As shown in Table 1, the comparison tests for hardness showed that the hardness of the catheter of Example 1 was 28% of the cold value whereas the hardness of the catheter of Comparison 1 was 25% of the cold value. In the tests for alcohol-resistance, the catheter of Example 1 could be flexed more than 500 times without cracking, whereas the catheter of Comparison 1 cracked after 182 deformations. These results confirm that there is no substantial difference in hardness by incorporating aromatic polyurethane in the cylindrical portion, but a very substantial improvement in alcohol-resistance.

Similar tests were made with Example 2 using a catheter in which the contrast-radiography linear portions were exposed at the surface of the transparent cylindrical portion. The catheter according to Example 2 was constructed as the catheter 10 of Example 1 except that the contrast-radiography linear portions were exposed at the surface of the cylindrical portion and had a circumferential extent of 58% of the circumference of the cylindrical portion, as shown in the following Table 2.

TABLE 2

| | Example 2 |
|---|---|
| Catheter Size | 16 G (external diameter: 1.50 mm) |
| Cylindrical Portion | Tecothane/Tecoflex = 60/40 |
| Contrast-Radiography Linear Portions | Tecoflex/barium sulfate = 60/40 |
| No. of Contrast-Radiography Linear Portions | 2 |
| Circumferential extent of Contrast-Radiography Linear Portions | 58% |
| Coating Yes-No/ Thickness | No |
| Hardness at 40° C. | 32% |
| Alcohol-Resistance | 428 times |

As shown in Table 2, the comparison test for hardness showed that the hardness of the catheter of Example 2 was 32% of the cold value, while in the test for alcohol-resistance the catheter of Example 2 could be flexed 428 times before a crack appeared. From these results it can be seen that, because the contrast-radiography linear portions were exposed, both the hardness and the alcohol-resistance were slightly inferior to those of the catheter of Example 1. As to alcohol-resistance, however, the result was far superior to that of Comparison 1. Moreover, the hardness was within a usable range although it was slightly higher than that of Comparison 1.

Similar tests were carried out on a catheter denoted as Comparison 2, the catheter of Comparison 2 having no transparent portion but being manufactured entirely from the material of the contrast-radiography linear portions. The catheter according to Comparison 2 was made of a material blended from an aromatic polymer sold under the Trade Mark Tecothane together with barium sulfate at a ratio of 80:20 (by weight or volume). The catheter had an external diameter equal to that of the foregoing embodiments. The results are shown in Table 3 below.

TABLE 3

| | Comparison 2 |
|---|---|
| Catheter Size | 16 G (external diameter: 1.50 mm) |
| Cylindrical Portion | — |
| Contrast-Radiography Linear Portions | Tecothane/barium sulfate = 80/20 |
| No. of Contrast-Radiography Linear Portions | Entire Area |
| Circumferential extent of Contrast-Radiography Linear Portions | — |
| Coating Yes-No/ Thickness | — |
| Hardness at 40° C. | 58% |
| Alcohol-Resistance | ≧500 times |

As shown in Table 3, in the catheter of Comparison 2 the hardness was 55% of the cold value, while in the test for alcohol-resistance the catheter of Comparison 2 could be flexed more than 500 times without a crack appearing. Because the catheter body was made exclusively of aromatic polyurethane and barium sulfate, it had an excellent alcohol-resistance but it had a high hardness value and consequently had lower bio-compatibility after being left in the patient's body.

It can be seen from these results that the catheters according to Examples 1 and 2 had superior chemical resistance (to carsinostatic, ethanol or the like) to the catheter of Comparison 1, as used in the prior art. It can also be seen that the catheters of Examples 1 and 2 had superior bodily softening characteristics to the catheter of Comparison 2, as used in the prior art. Moreover, the catheters according to Examples 1 and 2 facilitate an external confirmation of the passage of liquid chemical through the catheter body. Therefore, the catheter according to the present invention is particularly suitable for use in situations in which the catheter remains in a blood vessel.

The catheter according to the present invention may be modified from that shown and described with reference to FIGS. 1 and 2. For example, the ratio of aromatic polyurethane to aliphatic polyurethane forming the transparent portion 13 is said to be 60:40 (by weight or volume), but can be suitably modified. In order to cause the catheter to exhibit greater chemical resistance it may be desirable to raise the ratio of the aromatic polyurethane to more than 40% (by weight or volume). Alternatively, it may be preferred to choose the content of the aromatic polyurethane in the range from about 50% to about 80% (by weight or volume).

Moreover, the transparent portion 13 could be manufactured of 100% of aromatic polyurethane. In this case, it is preferred that the ratio of the aliphatic polyurethane of the materials forming the contrast-radiography linear portions 14a and 14b is increased. In this way the operability and the bio-compatibility can be improved, and the content of the barium sulfate can be increased so that a sufficient contrast-radiography can be maintained.

In the aforementioned embodiment, moreover, the contrast-radiography linear portions 14a and 14b are completely coated with the material of the transparent cylindrical portion 13. However, the contrast-radiography linear portions 14a and 14b could also be formed in an exposed manner. In this case, the two transparent portions and the two contrast-radiography linear portions are alternately arranged into a tubular shape. However, for greatest effectiveness, it may be preferable for the contrast-radiography linear portions to be coated with the material of the transparent cylindrical portion. In this way, chemical resistance is conferred by the aromatic polyurethane of the transparent portion, while the contrast-radiography and bodily softening characteristics are conferred by the aliphatic polyurethane.

Specifically, it is preferable that the contrast-radiography linear portions are coated with the material of the transparent portion. This has high chemical resistance so as to protect the contrast-radiography linear portions, which are mainly composed of aliphatic polyurethane which has lower chemical resistance. This enables the catheter to exhibit high contrast-radiography properties and good bodily softening characteristics in the contrast-radiography linear portions. The thickness of the transparent portion covering the contrast-radiography linear portions is preferably at least 0.01 mm and more preferably at least 0.02 mm. On the other hand, the circumferential extent (width) of the contrast-radiography linear portions is preferably within a range of from about 10% to about 70% of the circumference of the transparent cylindrical portion.

It is difficult to provide effective contrast-radiography if the circumferential extent (width) of the contrast-radiography linear portions is less than 10% of the circumference of the cylindrical portion, while it is difficult to observe the liquid passing through the catheter if the circumferential extent (width) of the contrast-radiography linear portions is greater than 70% of the circumference of the cylindrical portion. It is usual to provide one to four contrast-radiography linear portions, but the catheter according to the present invention may incorporate any convenient number of linear portions. In the aforementioned embodiment, on the other hand, the aromatic polyurethane is exemplified by material sold under the Trade Mark Tecothane, but can alternatively be exemplified by material sold under the Trade Mark Pellethane (Pharmacy Up-John Inc.) or material sold under the Trade Mark Miractran (Nippon Miractran Co., Ltd.).

The X-ray opaque agent can be exemplified not only by barium sulfate but also by bismuth subcarbonate, bismuth tungstate, tantalum tungstate or the like. In the aforementioned embodiment, the catheter 10 remains in the blood vessel, but the catheter according to the invention is not limited to such use, but can be applied to medical catheters in general. The described catheter has a relatively high hardness at the room temperature so that it is excellent in insertability, but the catheter softens in the body so that it does not damage the living body. Further, the catheter according to the present invention demonstrates excellent chemical resistance, especially resistance to alcohol.

The invention claimed is:

1. A catheter comprising:
   a tubular body portion including an elongate portion comprising a transparent material, the body portion being hollow to allow passage of a liquid therethrough; and
   at least one substantially linear contrast-radiography portion comprising an X-ray opaque material extending in the longitudinal direction of the elongate portion,
   wherein the transparent material comprises a mixture of an aromatic polyurethane and an aliphatic polyurethane, and the material forming the at least one contrast-radiography portion comprises a mixture of the X-ray opaque material and an aliphatic polyurethane.

2. The catheter of claim 1, wherein the at least one contrast-radiography portion is enclosed in a wall portion forming the elongate portion.

3. The catheter of claim 2, wherein the at least one contrast-radiography portion is embedded in the wall portion to a depth of at least 0.01 mm.

4. The catheter of claim 2, wherein the at least one contrast-radiography portion is embedded in the wall portion to a depth of at least 0.02 mm.

5. The catheter of claim 2, wherein the at least one contrast-radiography portion is embedded in the wall portion to a depth of about 0.04 mm.

6. The catheter of claim 1, wherein the transparent material forming the elongate portion comprises from about 50% to about 80% aromatic polyurethane.

7. The catheter of claim 1, wherein the transparent material forming the elongate portion comprises about 60% aromatic polyurethane.

8. The catheter of claim 1, wherein more than one contrast-radiography portion is provided.

9. The catheter of claim 8, wherein two contrast-radiography portions are provided.

10. The catheter of claim 1, wherein the at least one contrast-radiography portion comprises about 60% aliphatic polyurethane.

11. The catheter of claim 1, wherein the X-ray opaque material is selected from the group consisting of barium sulfate, bismuth subcarbonate, bismuth tungstate, tantalum tungstate and mixtures thereof.

12. The catheter of claim 1, wherein the contrast-radiography portion possesses a circumference from about 10% to about 70% of the circumference of the elongate portion.

13. The catheter of claim 1, wherein the contrast-radiography portion possesses a circumference about 60% of the circumference of the elongate portion.

14. A catheter comprising:
a tubular body portion including an elongate portion comprising a transparent material, the body portion being hollow to allow passage of a liquid therethrough; and
more than one substantially linear contrast-radiography portions comprising an X-ray opaque material extending in the longitudinal direction of the elongate portion,
wherein the transparent material comprises a mixture of an aromatic polyurethane and an aliphatic polyurethane, and the material forming the at least one contrast-radiography portion comprises a mixture of the X-ray opaque material and an aliphatic polyurethane.

15. The catheter of claim 14, wherein two contrast-radiography portions are provided.

* * * * *